(12) United States Patent
Crowley et al.

(10) Patent No.: US 11,524,128 B2
(45) Date of Patent: Dec. 13, 2022

(54) BLISTER PACK AND INHALER COMPRISING THE SAME

(71) Applicant: Norton (Waterford) Limited, Waterford (IE)

(72) Inventors: Peter John Crowley, Waterford (IE); Jan Geert Hazenberg, Kilkenny (IE); Daniel Buck, Waterford (IE); Christopher David Edlin, Waterford (IE); Hardik Kirtikumar Shah, Waterford (IE)

(73) Assignee: NORTON (WATERFORD) LIMITED, Waterford (IE)

( * ) Notice: Subject to any disclaimer, the term of this patent is extended or adjusted under 35 U.S.C. 154(b) by 0 days.

(21) Appl. No.: 17/366,906

(22) Filed: Jul. 2, 2021

(65) Prior Publication Data

US 2021/0386946 A1    Dec. 16, 2021

Related U.S. Application Data

(63) Continuation of application No. PCT/EP2021/066130, filed on Jun. 15, 2021.

(30) Foreign Application Priority Data

Jun. 15, 2020 (GB) ...................... 2009054

(51) Int. Cl.
*A61M 15/00* (2006.01)

(52) U.S. Cl.
CPC .... *A61M 15/0051* (2014.02); *A61M 15/0003* (2014.02); *A61M 15/0021* (2014.02); *A61M 2202/064* (2013.01)

(58) Field of Classification Search
CPC .......... A61M 15/0051; A61M 15/0003; A61M 15/0021; A61M 2202/06; A61M 15/0045;
(Continued)

(56) References Cited

U.S. PATENT DOCUMENTS

2003/0075172 A1* 4/2003 Johnson ................... A61P 9/12
128/200.24
2004/0258625 A1* 12/2004 Nilsson ............. A61M 15/0051
424/46
(Continued)

FOREIGN PATENT DOCUMENTS

GB          2242134 A      9/1991
WO     2003/061744 A1     7/2003
(Continued)

OTHER PUBLICATIONS

International Search Report for PCT/EP2021/066130; dated Sep. 30, 2021; 12 pages.
(Continued)

*Primary Examiner* — Justine R Yu
*Assistant Examiner* — Matthew R Moon
(74) *Attorney, Agent, or Firm* — Morgan, Lewis & Bockius LLP

(57) ABSTRACT

Provided is a blister pack for a dry powder inhaler configured to deliver a first powder medicament and a second powder medicament different from the first powder medicament. The first and second powder medicaments are contained within blister pockets defined in a strip. A series of blister pockets is defined in the strip, which series extends linearly along the length of the strip. The first and second powder medicaments are contained in blister pockets of the series. Alternatively or additionally, each of the blister pockets is elongated such as to have a largest dimension parallel with the length of the strip. These measures, either individually or in combination, enable minimizing of the width of the strip in spite of the strip accommodating both the first and second powder medicaments.

18 Claims, 6 Drawing Sheets

(58) Field of Classification Search
CPC .......... A61M 15/0046; A61M 15/0048; A61M 15/005
See application file for complete search history.

(56) References Cited

U.S. PATENT DOCUMENTS

| | | |
|---|---|---|
| 2005/0147566 A1 | 7/2005 | Fleming et al. |
| 2008/0274188 A1* | 11/2008 | Alexander ........... A61K 9/0056 424/484 |
| 2011/0277753 A1 | 11/2011 | Dunne et al. |
| 2020/0324064 A1* | 10/2020 | Huang .............. A61M 15/0003 |

FOREIGN PATENT DOCUMENTS

| | | |
|---|---|---|
| WO | 2007/012871 A1 | 2/2007 |
| WO | 2007/068900 A3 | 6/2007 |
| WO | 2007068896 A1 | 6/2007 |
| WO | 2007/129127 A1 | 11/2007 |
| WO | 2009/092520 A1 | 7/2009 |
| WO | 2010/133321 A1 | 11/2010 |
| WO | 2010/133323 A1 | 11/2010 |
| WO | 2010/136134 A1 | 12/2010 |
| WO | 2020/053878 A1 | 3/2020 |

OTHER PUBLICATIONS

International Search Report for GB 20009054.4; dated Dec. 4, 2020; 5 pages.

* cited by examiner

BLISTER PACK AND INHALER COMPRISING THE SAME

CROSS REFERENCE TO RELATED APPLICATIONS

This application is a Continuation of International Patent Application No. PCT/EP2021/066130 filed Jun. 15, 2021, entitled "Blister Pact and Inhaler Comprising the Same", which claims the benefit of GB Patent Application No. 2009054.4 filed Jun. 15, 2020, entitled "Blister Pack and Inhaler Comprising the Same", each of which is incorporated by reference herein in its entirety.

FIELD OF THE INVENTION

This invention relates to blister packs for dry powder inhalers, and dry powder inhalers comprising the blister packs.

BACKGROUND OF THE INVENTION

Inhalers for drug delivery to a patient by inhalation are well-known. Such devices include metered-dose inhalers and dry powder inhalers.

Metered dose inhalers typically comprise a container containing a propellant and a liquid solution or suspension of a medicament. Metered dose inhalers further include a dispensing valve which, when actuated, causes the medicament to be forced out of the container by expansion of the propellant in the form of an aerosol.

Dry powder inhalers, on the other hand, typically contain a stock of the medicament in dry powder form, and are arranged to permit the subject to inhale discrete doses from the stock of powder medicament.

In some cases, it is desirable for the inhaler to deliver combinations of different medicaments to the subject. This can present a challenge in terms of how to store and deliver the medicaments. This is a particular challenge in the case of dry powder inhalers because it may be difficult to minimize or prevent unwanted reactions or interactions between the powder medicaments prior to delivery to the subject.

This problem may be addressed by storing the doses of the powder medicaments in respective blisters pockets defined in a strip or strips of a blister pack, and using a known inhaler design which enables release of the powder medicaments by piercing, rupturing or peeling a portion of a cover of the strip just before the dose is to be delivered to the patient for inhalation.

However, providing blister pockets containing more than one powder medicament type in this manner may reduce the compactness of the inhaler, which may discourage the subject from carrying the inhaler with them. Thus, the inhaler may not be available when it is required.

Moreover, there is a growing desire to incorporate use detection and wireless connectivity electronics in the inhaler, to assist with use and compliance monitoring. However, including blister pockets containing different medicaments within the inhaler may provide an obstacle for incorporating such features in the inhaler, because the compactness of the inhaler would be yet further reduced.

SUMMARY OF THE INVENTION

The invention is defined by the claims.

According to a first aspect there is provided a dry powder inhaler configured to deliver a first powder medicament and a second powder medicament different from the first powder medicament, the dry powder inhaler comprising: a blister pack; and a medicament delivery assembly, wherein the blister pack comprises: a strip in which blister pockets are defined, said first and second powder medicaments being contained within the blister pockets, wherein a series of blister pockets is defined in the strip, the series extending linearly along the length of the strip, wherein the first and second powder medicaments are respectively contained in consecutive blister pockets of the series, such that the blister pockets containing the first powder medicament alternate with the blister pockets containing the second powder medicament along the length of the strip, wherein the blister pack further comprises a peelable cover for covering the blister pockets, wherein the blister pockets are defined in a base layer, and wherein the peelable cover is releasably adhered to the base layer between the blister pockets, and wherein the medicament delivery assembly is configured to: access the blister pockets and permit a subject to inhale the first and second powder medicaments therefrom, wherein the medicament delivery assembly is configured to permit the subject to inhale the first and second powder medicaments simultaneously, the medicament delivery assembly being configured to access consecutive blister pockets for each inhalation using the inhaler, wherein the medicament delivery assembly comprises a peeling mechanism configured to peel the cover covering a pair of consecutive blister pockets thereby to expose the first and second powder medicaments for each inhalation using the inhaler.

By containing the first and second powder medicaments in alternating blister pockets of the same series, the width of the strip may be minimized in spite of the strip accommodating both the first and second powder medicaments. Such minimizing of the width of the strip may, in turn, enable the depth/thickness of the dry powder inhaler to be minimized, and/or additional space to be provided in the dry powder inhaler for accommodating, for example, use detection and wireless connectivity electronics for sending use detection data to an external device, such as a smartphone.

The medicament delivery assembly is nonetheless configured to access consecutive blister pockets, thereby permitting the subject to inhale both medicaments in a single inhalation. Thus, the dry powder inhaler can combine compactness with convenience of combined medicament administration.

The medicament delivery assembly comprises a peeling mechanism configured to peel the cover covering a pair of consecutive blister pockets thereby to expose the first and second powder medicaments for each inhalation using the inhaler. This may provide a convenient way of accessing the consecutive blister pockets which can also make for consistent and reliable simultaneous delivery of the first and second powder medicaments.

The dry powder inhaler may further comprise a mouthpiece. The medicament delivery assembly may comprise a manifold configured such that the first and second powder medicaments from the accessed consecutive blister pockets are drawn simultaneously therethrough and out of the mouthpiece when the subject inhales through the mouthpiece.

The manifold may comprise a first flow path along which the first powder medicament is carried towards the mouthpiece from one of the accessed consecutive blister pockets, and a second flow path along which the second powder medicament is carried towards the mouthpiece from the other of the accessed consecutive blister pockets. This may facilitate simultaneous inhalation of the first and second powder medicaments.

The first and second flow paths may, for example, meet with each other at a point upstream of the mouthpiece.

Such a manifold may not require any movement of the manifold, nor movement of any part of the manifold, relative to the consecutive blister pockets during the inhalation.

According to a second aspect there is provided a dry powder inhaler configured to deliver a first powder medicament and a second powder medicament different from the first powder medicament, the dry powder inhaler comprising: a blister pack; and a medicament delivery assembly, wherein the blister pack comprises: a strip in which blister pockets are defined, said first and second powder medicaments being contained within the blister pockets, wherein a series of blister pockets is defined in the strip, the series extending linearly along the length of the strip, wherein each of the blister pockets is divided into a first pocket portion containing the first powder medicament, and a second pocket portion containing the second powder medicament, the first pocket portion adjoining the second pocket portion at a pinch point for restricting combining of the first and second powder medicaments with each other, wherein the blister pack further comprises a peelable cover for covering the blister pockets, wherein the blister pockets are defined in a base layer, and wherein the peelable cover is releasably adhered to the base layer between the blister pockets, and wherein the medicament delivery assembly is configured to: access the blister pockets and permit a subject to inhale the first and second powder medicaments therefrom, wherein the medicament delivery assembly is configured to permit the subject to inhale the first and second powder medicaments simultaneously, the medicament delivery assembly being configured to access the first and second pocket portions for each inhalation using the inhaler, wherein the medicament delivery assembly comprises a peeling mechanism configured to peel the cover covering the first and second pocket portions thereby to expose the first and second powder medicaments for each inhalation using the inhaler.

This aspect provides an alternative solution to the same problem(s) addressed by the above-described first aspect. In particular, by containing the first and second powder medicaments in respective pocket portions of the same blister pocket, the compactness of the blister pack and thus the dry powder as a whole may be improved, e.g. to enable additional space to be provided in the dry powder inhaler for accommodating, for example, use detection and wireless connectivity electronics for sending use detection data to an external device, such as a smartphone.

The medicament delivery assembly is nonetheless configured to access both the first and second pocket portions, thereby permitting the subject to inhale both medicaments in a single inhalation. Thus, the dry powder inhaler can combine compactness with convenience of combined medicament administration.

The medicament delivery assembly comprises a peeling mechanism configured to peel the cover covering the first and second pocket portions thereby to expose the first and second powder medicaments for each inhalation using the inhaler. This may provide a convenient way of accessing the pocket portions which can also make for consistent and reliable simultaneous delivery of the first and second powder medicaments.

The first pocket portion may be at a different position along the length of the strip from the second pocket portion.

Alternatively or additionally, the first pocket portion may contain a different volume of the first powder medicament from that of the second powder medicament contained by the second pocket portion.

The dry powder inhaler may further comprise a mouthpiece. The medicament delivery assembly may comprise a manifold configured such that the first and second powder medicaments from the accessed first and second pocket portions are drawn simultaneously therethrough and out of the mouthpiece when the subject inhales through the mouthpiece.

The manifold may comprise a first flow path along which the first powder medicament is carried towards the mouthpiece from one of the pocket portions, and a second flow path along which the second powder medicament is carried towards the mouthpiece from the other of the pocket portions. This may facilitate simultaneous inhalation of the first and second powder medicaments.

The first and second flow paths may, for example, meet with each other at a point upstream of the mouthpiece.

Such a manifold may not require any movement of the manifold, nor movement of any part of the manifold, relative to the first and second pocket portions during the inhalation.

According to a third aspect there is provided a dry powder inhaler configured to deliver a first powder medicament and a second powder medicament different from the first powder medicament, the dry powder inhaler comprising: a blister pack; and a medicament delivery assembly, wherein the blister pack comprises: a strip in which a series and a further series of blister pockets are defined, wherein the series and further series are parallel with each other and extend along the length of the strip, the first powder medicament being contained in the blister pockets of the series, and the second powder medicament being contained in the blister pockets of the further series, wherein the strip is friable along a friable portion extending along at least part of the length of the strip between the series and the further series, wherein the strip is foldable along said friable portion, wherein the medicament delivery assembly is configured to: separate the series from the further series along the friable portion, wherein the medicament delivery assembly is configured to separate the series from the further series while the strip is folded along the friable portion; and access the blister pockets and permit a subject to inhale the first and second powder medicaments therefrom.

The friable portion may facilitate delivery of the respective powder medicaments within the dry powder inhaler. The blister pockets of the series may all protrude in the same direction as each other. Similarly, the blister pockets of the further series may all protrude in the same direction as each other. This may mean that, in the case of the folded strip, the blister pockets of the series protrude in a different, e.g. opposite, direction from the blister pockets of the further series.

The term "friable portion" is intended to mean that this portion of the strip is weaker, for example more easily broken or cut, than other areas of the strip. Accordingly, the strip may be preferentially divided along the friable portion. Dividing the strip along the friable portion may not itself cause opening of the blister pockets of the series and the further series.

The medicament delivery assembly may be configured to access at least one of said blister pockets of the series and at least one of said blister pockets of the further series for each inhalation using the inhaler. This may facilitate simultaneous inhalation of the first and second powder medicaments.

The medicament delivery assembly may, for example, be configured to separate the series from the further series prior to accessing the respective blister pockets of the series and the further series.

According to a fourth aspect there is provided a dry powder inhaler configured to deliver a first powder medicament and a second powder medicament different from the first powder medicament, the dry powder inhaler comprising: a blister pack; and a medicament delivery assembly, wherein the blister pack comprises: a first base layer in which a series of blister pockets are defined, and a second base layer in which a further series of blister pockets are defined, the first powder medicament being contained in the blister pockets of the series, and the second powder medicament being contained in the blister pockets of the further series, wherein the blister pack further comprises a unitary cover for covering the blister pockets of the series and the further series, wherein the unitary cover comprises a first surface and a second surface facing away from the first surface, the blister pockets of the series are covered by the first surface of the unitary cover, and the blister pockets of the further series are covered by the second surface of the unitary cover, wherein the medicament delivery assembly is configured to: access the blister pockets and permit a subject to inhale the first and second powder medicaments therefrom.

The term "unitary cover" is intended to mean that all layers of the cover are permanently attached to each other, other than layers of adhesive present on the outermost surfaces. The term "unitary cover" accordingly excludes covers formed from two separate covers which are releasably joined to each other. A single unitary cover can assist to increase the compactness of the dry powder inhaler by (at least) decreasing the thickness of the strip relative to the scenario in which the series and further series of blister pockets of the first and second base layers are each covered by their own cover.

The blister pockets of the series may be aligned with the blister pockets of the further series, or the blister pockets of the series may be offset relative to the blister pockets of the further series. Both of these scenarios are possible due, at least in part, to the unitary cover.

In an embodiment, the unitary cover is a peelable cover, and the first surface is releasably adhered to the first base layer between the blister pockets of the series, and the second surface is releasably adhered to the second base layer between the blister pockets of the further series, and wherein the medicament delivery assembly comprises a peeling mechanism configured to peel the first base layer and the second base layer from the unitary cover thereby to expose the first and second powder medicaments.

Peeling the unitary cover from both the first and second base layers can provide a convenient way of accessing the blister pockets. The peeling mechanism can, for example, be configured to peel the first base layer and the second base layer simultaneously from the unitary cover. Alternatively, the peeling mechanism can be configured to peel the first base layer from the unitary cover and then peel the second base layer from the unitary cover (or peel the second base layer from the unitary cover and then peel the first base layer from the unitary cover) sequentially.

In other examples, the blister pockets of the series and the further series can be accessed via a suitable rupturing, puncturing and/or tearing mechanism included in the medicament delivery assembly.

According to a fifth aspect there is provided is a blister pack for a dry powder inhaler configured to deliver a first powder medicament and a second powder medicament different from the first powder medicament, the blister pack comprising: a strip in which blister pockets are defined, the first and second powder medicaments being contained within the blister pockets, wherein a series of blister pockets is defined in the strip, the series extending linearly along the length of the strip, wherein the first and second powder medicaments are contained in blister pockets of the series; and/or each of the blister pockets is elongated such as to have a largest dimension parallel with the length of the strip.

By containing the first and second powder medicaments in blister pockets of the same series, the width of the strip may be minimized in spite of the strip accommodating both the first and second powder medicaments. The blister pockets of the series may all protrude in the same direction as each other. As an alternative solution, or in addition to containing the first and second powder medicaments in blister pockets of the same series, each of the blister pockets in the strip is elongated such as to have a largest dimension parallel with the length of the strip. This measure may also assist to minimize the width of the strip, whilst ensuring that sufficient volume is provided in the blister pockets to contain the requisite quantities of the first and second powder medicaments.

Such minimizing of the width of the strip may, in turn, enable the depth/thickness of the dry powder inhaler to be minimized, and/or additional space to be provided in the dry powder inhaler for accommodating, for example, use detection and wireless connectivity electronics for sending use detection data to an external device, such as a smartphone.

The first and second powder medicaments may be respectively contained in consecutive blister pockets of the series, such that the blister pockets containing the first powder medicament alternate with the blister pockets containing the second powder medicament along the length of the strip. This arrangement may facilitate simultaneous inhalation of the first and second powder medicaments using the dry powder inhaler, particularly in examples in which a medicament delivery assembly of the dry powder inhaler is configured to access a pair of the consecutive blister pockets by peeling a peelable cover to expose first and second dry powder medicaments contained in the pair of consecutive blister pockets.

In an embodiment, for each pair, the pocket containing the first powder medicament and the pocket containing the second powder medicament overlap each other in the length direction. This may provide a particularly space efficient arrangement of the blister pockets in the strip.

The width of the blister pocket containing the first powder medicament may, for example, decrease in the direction of the length of the strip as the width of the blister pocket containing the second powder medicament increases. This may, for example, lead to an overall width of the blister pockets, defined by the sum of the widths of the blister pockets of the pair, being substantially constant in the region of overlap.

When, for example, a peelable cover covers the pair of blister pockets, a relatively constant peeling force may therefore be used in order to expose the first and second powder medicaments contained in the blister pockets of the pair. Thus, opening of the pair of blister pockets by a peeling mechanism included in a medicament delivery assembly of the dry powder inhaler may be facilitated.

When the first and second powder medicaments are both contained in the blister pockets of the series, each of the blister pockets may be elongated such as to have a largest dimension parallel with the width of the strip. Containing the first and second powder medicaments in blister pockets of the same series may compensate for arranging the blister pockets such that their largest dimension is parallel with the width of the strip, in other words perpendicular to the length of the strip.

In another set of examples, each of the blister pockets of the strip is elongated such as to have a largest dimension parallel with the length of the strip. This may assist to minimize the width of the strip, whilst ensuring that sufficient volume is provided in the blister pockets to contain the requisite quantities of the first and second powder medicaments, as previously described.

Each of the blister pockets may, for example, be divided into a first pocket portion containing the first powder medicament, and a second pocket portion containing the second powder medicament. In this example, the first pocket portion adjoins the second pocket portion at a pinch point for restricting combining of the first and second powder medicaments with each other.

The first and second powder medicaments being contained in adjacent pocket portions of the same blister pocket may facilitate simultaneous delivery of the first and second powder medicaments therefrom during an inhalation using the dry powder inhaler.

The first pocket portion may be at a different position along the length of the strip from the second pocket portion. Alternatively or additionally, the first pocket portion may contain a different volume of the first powder medicament from that of the second powder medicament contained by the second pocket portion. In this way, the respective volumes of the pocket portions may be adjusted according to the dose strengths of the first and second powder medicaments which are to be delivered to the subject.

More generally, the strip may, for example, comprise 30 to 120, such as 40 to 110, e.g., 60 to 100, doses of the first powder medicament. Thus, the strip may comprise 30 to 120, such as 40 to 110, e.g., 60 to 100, blister pockets or first pocket portions containing the first powder medicament.

Similarly, the strip may, for instance, comprise 30 to 120, such as 40 to 110, e.g., 60 to 100, doses of the second powder medicament. Thus, the strip may comprise 30 to 120, such as 40 to 110, e.g., 60 to 100, blister pockets or second pocket portions containing the second powder medicament.

In a further set of examples, the strip comprises a further series of blister pockets, the further series extending linearly along the length of the strip. In such examples, each of the blister pockets of the series and the further series is elongated such as to have a largest dimension parallel with the length of the strip.

The largest dimension of the blister pockets being parallel with the length of the strip for both the series and the further series may assist to minimize the width of the strip in spite of the strip comprising a plurality of series of blister pockets.

The first powder medicament may be contained in the blister pockets of the series, and the second powder medicament may be contained in the blister pockets of the further series. This may, for example, facilitate manufacturing of the strip. For example, the first powder medicament may be dispensed into the blister pockets of the series defined in a first precursor strip, and the second powder medicament may be dispensed into the blister pockets of the further series defined in a second precursor strip, followed by joining of the first and second precursor strips together along their respective lengths to form the strip.

At least part of each of the blister pockets of the series may be aligned with a respective blister pocket of the further series. This may, for example, facilitate simultaneous inhalation of both the first and second powder medicaments using the dry powder inhaler.

As used herein the terms "series" and "further series" each refer to a single line or single row of blister pockets extending along the length of the strip. As such, the term "series", when used in the singular, e.g. "a series", is not intended to cover a matrix of blister pockets in which the blister pockets are arranged in a plurality of rows, with each row extending along the length of the strip. By which we mean that the term "a series" does not cover a plurality of columns of blister pockets, which columns are spaced from each other along the length of the strip, the centers of the blister pockets in each column being, for instance, aligned on a transverse line parallel with the width of the strip.

A medicament delivery assembly of a dry powder inhaler may, for instance, access one of the blister pockets of the series and, at the same time, an aligned blister pocket of the further series for each inhalation using the inhaler. Such accessing may, for example, be effected by peeling a peelable cover to expose the blister pocket of the series and the aligned blister pocket of the further series for each inhalation.

According to a sixth aspect there is provided a blister pack for a dry powder inhaler configured to deliver a first powder medicament and a second powder medicament different from the first powder medicament, the blister pack comprising: a strip in which a series and a further series of blister pockets are defined, wherein the series and further series are parallel with each other and extend along the length of the strip, the first powder medicament being contained in the blister pockets of the series, and the second powder medicament being contained in the blister pockets of the further series, wherein the strip is friable along a friable portion extending along at least part of the length of the strip between the series and the further series.

The friable portion may facilitate delivery of the respective powder medicaments within the dry powder inhaler. A medicament delivery assembly included in the inhaler may, for example, separate the series and the further series, and, for each inhalation, access the blister pocket containing the first powder medicament from the series, and separately access the blister pocket containing the second powder medicament from the further series.

The blister pockets of the series may all protrude in the same direction as each other. Similarly, the blister pockets of the further series may all protrude in the same direction as each other.

The term "friable portion" is intended to mean that this portion of the strip is weaker, for example more easily broken or cut, than other areas of the strip. Accordingly, the strip may be preferentially divided along the friable portion. Dividing the strip along the friable portion may not itself cause opening of the blister pockets of the series and the further series.

The blister pack of this sixth aspect may have any of the features, where applicable, of the blister pack according to any of the aspects described above. For example, the blister pockets of the blister pack of this aspect may have the shape and/or orientation of the blister pockets described above in relation to any of the above-described aspects. Similarly, features of the blister pack of this sixth aspect, such as the friable portion, may, where applicable, be incorporated in embodiments of the blister pack of any of the above-described aspects.

Manufacturing of the strip may, for example, comprise dispensing the first powder medicament into the blister pockets of the series defined in a first precursor strip, and the second powder medicament may be dispensed into the blister pockets of the further series defined in a second precursor strip, followed by joining of the first and second precursor strips together along their respective lengths. This has the advantage of minimizing contamination of the first powder medicament with the second powder medicament, and vice versa, during manufacturing of the blister pack.

The friable portion may be provided, for instance, by the manner in which the first and second precursor strips are joined together. Alternatively, the friable portion may be provided in a separate step before or after joining the first and second precursor strips together. The friable portion may, for example, comprise or consist of a perforation in the strip extending between the series and the further series along the length of the strip.

The strip may, for example, be foldable along the friable portion. This may assist to increase the compactness of the dry powder inhaler containing the blister pack, since the strip may be folded inside the dry powder inhaler prior to accessing of the blister pockets by the medicament delivery assembly included in the inhaler.

More generally, the blister pockets containing the first powder medicament may be joined to the blister pockets containing the second powder medicament. This may, for example, involve joining blocks or series of blister pockets to further blocks or further series of blister pockets. It is also conceivable that individual blister pockets define the units which are joined to each other in order to provide the strip.

Alternatively, the blister pockets containing the first powder medicament and the blister pockets containing the second powder medicament may be integrally formed in the strip.

The blister pack according to any of the above-described examples may further comprise a peelable cover for covering the blister pockets, wherein the blister pockets are defined in a base layer, and wherein the peelable cover is releasably adhered to the base layer between the blister pockets. Such a peelable cover-base layer arrangement may facilitate manufacturing of the blister pack, as well as providing a convenient way for the medicament delivery assembly of a dry powder inhaler to access the dry powder medicaments contained in the blister pockets.

Further provided is a dry powder inhaler comprising: the blister pack as defined above in respect of the fifth and sixth aspects; and a medicament delivery assembly configured to access the blister pockets and permit a subject to inhale the first and second powder medicaments therefrom.

The medicament delivery assembly may be configured to permit the subject to inhale the first and second powder medicaments simultaneously. This may be particularly preferred when the first and second powder medicaments are for combined maintenance and rescue therapy.

The medicament delivery assembly may be configured to access consecutive blister pockets for each inhalation using the inhaler.

The medicament delivery assembly may comprise, when the blister pockets are covered by the peelable cover, a peeling mechanism configured to peel the cover thereby to expose the first and second powder medicaments for each inhalation using the inhaler.

In examples in which the blister pockets are elongated, the medicament delivery assembly may be configured such that at least one of the elongated blister pockets is accessed for each inhalation using the inhaler.

In examples in which the blister pockets are defined in the series and the further series, the medicament delivery assembly may be configured to access at least one of the blister pockets of the series and at least one of the blister pockets of the further series for each inhalation using the inhaler.

In examples in which the blister pockets are defined in the series and the further series, and the series and the further series are separated by the friable portion, the medicament delivery assembly may be configured to separate the series from the further series along the friable portion.

The medicament delivery assembly may, for example, be configured to separate the series from the further series of blister strips prior to accessing the respective blister pockets of the series and the further series. In a particular example in which the series and the further series are foldable along the friable portion, the medicament delivery assembly may be configured to separate the series from the further series while the strip is folded along the friable portion.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1A:
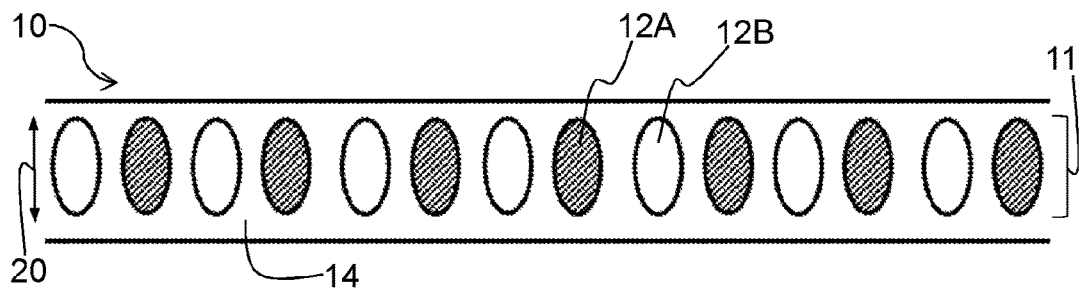
FIG. 1A shows a plan view of a strip of a blister pack according to an example.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Provided is a blister pack for a dry powder inhaler, which dry powder inhaler is configured to deliver a first powder medicament and a second powder medicament different from the first powder medicament. The first and second powder medicaments are contained within blister pockets defined in a strip. A series of blister pockets is defined in the strip, which series extends linearly along the length of the strip. The first and second powder medicaments are contained in blister pockets, e.g. respective blister pockets, of the series. Alternatively or additionally, each of the blister pockets is elongated such as to have a largest dimension parallel with the length of the strip. These measures, either individually or in combination, enable minimizing of the width of the strip in spite of the strip accommodating both the first and second powder medicaments. This, in turn, may enable the depth/thickness of the dry powder inhaler to be minimized, and/or additional space to be provided inside the dry powder inhaler for accommodating, for example, use detection and wireless connectivity electronics for sending use detection data to an external device, such as a smartphone.

Providing the first and second powder medicaments within the same blister strip may offer various advantages over, for example, solutions involving a plurality of separate strips, with the first powder medicament being contained in the blister pockets of one of the strips, and the second powder medicament being contained in the blister pockets of a separate strip. In such separate strip solutions, a single driving mechanism in the dry powder inhaler may advance the separate strips and access the respective blister pockets. Dose counting may thus, for example, rely on an inherent assumption that both blister pockets of the separate strips have been advanced and accessed upon each actuation. By providing the first and second powder medicaments within the blister pockets of the same strip, more reliable confirmation may be attained, via, for instance, a dose counter included in the dry powder inhaler, that both the first and second powder medicaments have been made available to the subject for each actuation.

Moreover, a strip having respective blister pockets for both the first and second powder medicaments may assist, for example, to reduce variability of blister pocket forming relative to the scenario in which the first and second powder medicaments are respectively contained blister pockets of separate strips.

First, second, and third powder medicaments which are all different from each other may, for example, be contained within the blister pockets of the same strip.

FIG. 1A shows a portion of a strip 10 of a blister pack according to a non-limiting example. The strip 10 comprises blister pockets 12A, 12B which contain a first powder medicament and a second powder medicament. The first powder medicament is different from the second powder medicament. The strip 10 may, for example, be used to provide a combination therapy to a subject.

In a non-limiting example, the first powder medicament is budesonide and the second powder medicament is formoterol (fumarate). In another example, the first powder medicament is beclomethasone (dipropionate), and the second powder medicament is formoterol (fumarate). In yet another example, the first powder medicament is fluticasone (propionate or furoate), and the second powder medicament is salmeterol (xinafoate).

In still another example, the first powder medicament is fluticasone (propionate or furoate) and the second powder medicament is albuterol (sulfate).

In further examples, the first powder medicament comprises fluticasone (furoate) and the second powder medicament comprises vilanterol (trifenatate); or the first powder medicament comprises umeclidinium (bromide) and the second powder medicament comprises vilanterol (trifenatate); or the first powder medicament comprises two selected from umeclidinium (bromide), fluticasone (furoate) and vilanterol (trifenatate), and the second powder medicament comprises the remaining medicament from umeclidinium (bromide), fluticasone (furoate) and vilanterol (trifenatate) not selected for the first powder medicament.

Parentheses indicate preferred salt or ester forms.

In such examples, the strip 10, in combination with a dry powder inhaler which delivers the first and second powder medicaments stored in the respective blister pockets 12A, 12B of the strip 10, may be used to provide maintenance and rescue therapy (MART).

More generally, the first and second powder medicaments may both be inhaled medicaments. For example, the first and second powder medicaments may both be inhaled medicaments suitable for treating a respiratory disease, such as asthma or chronic obstructive pulmonary disease.

The blister pockets 12A containing the first powder medicament are distinguished from the blister pockets 12B containing the second powder medicament in FIG. 1A by the hatching used for the latter but not the former. Separately storing the first powder medicament and the second powder medicament in this manner may minimize the risk of any unwanted reactions and/or interactions occurring between the first and second powder medicaments, or components of their respective dry powder formulations, prior to the subject inhaling the powder medicaments.

The blister pockets 12A, 12B may take the form of cavities or recesses formed in a base layer 14. The strip 10 may, for example, be formed by a cold-forming or thermoforming process. In the thermoforming process a polymeric base layer 14 is softened at an elevated temperature and forced onto a negative mold having protrusions which define the shape of the cavities. In the cold-forming process, a laminate base layer 14 film, e.g. comprising an aluminum foil layer, is pressed into a mold by means of a stamp. Suitable methods of manufacturing strips 10 having blister pockets 12A, 12B defined therein are well-known per se, and will not be further discussed herein for the sake of brevity only.

Figure 1B:
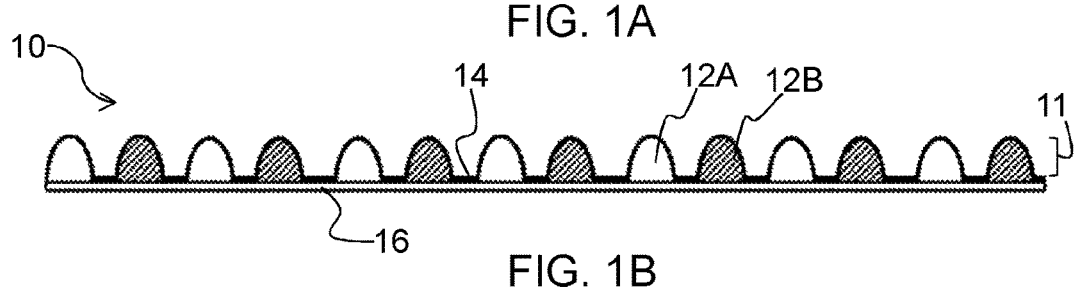
FIG. 1B shows a side view of the strip shown in FIG. 1A.

FIG. 1B provides a side view of the strip 10 shown in FIG. 1A. As well as showing bulging of the blister pockets 12A, 12B relative to regions of the base layer lying between the blister pockets 12A, 12B, FIG. 1B shows a cover 16 which covers the blister pockets 12A, 12B. The cover 16 may be alternatively termed a "lid" because of its function of retaining the dry powder medicaments within the blister pockets 12A, 12B.

The cover 16 may be adhered to the regions of the base layer 14 lying between the blister pockets 12A, 12B. In a non-limiting example, the cover 16 is a peelable cover 16. In such an example, the peelable cover 16 is releasably adhered to the regions of the base layer 14 lying between the blister pockets 12A, 12B. The dry powder inhaler (not visible in FIGS. 1A and 1B) in which the blister pack is incorporated may be configured to peel the peelable cover 16 from the base layer 14, as will be described in more detail herein below with reference to FIGS. 7C, 7D and 9.

In other examples, the cover 16 may not be peelable from the base layer 14, but the dry powder inhaler may nevertheless be configured to access the blister pockets 12A, 12B, for example by rupturing, puncturing or tearing the blister pockets 12A, 12B.

The cover 16 may, for instance, hermetically seal the first and second powder medicaments in their respective blister pockets. In this way, air, and in particular the moisture present in the air, may be prevented by the cover 16 from accessing the interior of the blister pockets 12A, 12B. Degradation of the dry powder medicaments contained within the blister pockets 12A, 12B by ambient air may be correspondingly minimized or prevented.

The cover 16 may be formed of any suitable material, for example a metallic foil, such as aluminum foil. One or more layers, such as a paper layer, may be adhered to the foil to strengthen the cover 16. The foil may be adhered to, e.g. releasably adhered to, the base layer 14 in any suitable manner, such as with a heat seal lacquer.

In the example shown in FIGS. 1A and 1B, the first and second powder medicaments are contained in blister pockets 12A, 12B of a linear series 11 of blister pockets 12A, 12B. As shown in FIG. 1B, the blister pockets 12A, 12B of the series 11 may all protrude in the same direction as each other.

The first and second powder medicaments being contained in blister pockets 12A, 12B belonging to the same linear series 11 may assist to minimize the width of the strip 10.

The blister pockets 12A containing the first powder medicament may, for instance, be integrally formed with the blister pockets 12B containing the second powder medicament in the strip 10. In such an example, filling of the blister pockets 12A, 12B with the first and second powder medicaments may comprise using a first dispenser to dispense the first powder medicament into the blister pockets 12A of the strip 10, and using a second dispenser to dispense the second powder medicament into the blister pockets 12B of the strip 10.

The dispensers may, for example, each comprise a nozzle, e.g. having a diameter in the range 0.9 mm to 1.3 mm, for directing the respective powder medicament into the blister pockets 12A, 12B.

In an alternative non-limiting example, the blister pockets 12A containing the first powder medicament are joined to the blister pockets 12B containing the second powder medicament. In this example, the blister pockets 12A, 12B may be filled with the respective powder medicament and the filled blister pockets 12A, 12B may be subsequently joined to each other, thereby to afford the strip 10. This may have the advantage of permitting the first and second powder medicaments to be kept separate from each other. In this way, the risk of contamination of the first powder medicament with the second powder medicament, and vice versa, may be minimized.

A cover portion may cover the blister pockets 12A following filling with the first powder medicament, and a further cover portion may cover the blister pockets 12B following filling with the second powder medicament. Once the blister pockets 12A, 12B are joined to each other, the cover portion and the further cover portion may define the cover 16. In other examples, the blister pockets 12A, 12B may be joined to each other prior to a single cover 16 covering the joined blister pockets 12A, 12B.

In the example shown in FIGS. 1A and 1B, the first and second powder medicaments are respectively contained in consecutive blister pockets 12A, 12B of the series 11. This arrangement means that the blister pockets 12A containing the first powder medicament alternate with the blister pockets 12B containing the second powder medicament along the length of the strip 10. This arrangement may facilitate simultaneous inhalation of the first and second powder medicaments using the dry powder inhaler, for example when the first and second powder medicaments are for MART.

The blister pocket 12A containing the first powder medicament may, for instance, be spaced sufficiently close to the consecutive, in other words adjacent, blister pocket 12B containing the second powder medicament such that the dry powder inhaler may access both of the consecutive blister pockets 12A, 12B, and enable the subject to inhaler the first powder medicament and the second powder medicament therefrom during the same inhalation using the inhaler.

The blister pockets 12A, 12B may have any suitable shape. Whilst the blister pockets 12A, 12B are oval shaped in the plan view provided in FIG. 1A, other shapes are conceivable. In the non-limiting example of FIG. 2, the blister pockets 12A, 12B are triangular in the plan view.

Figure 2:
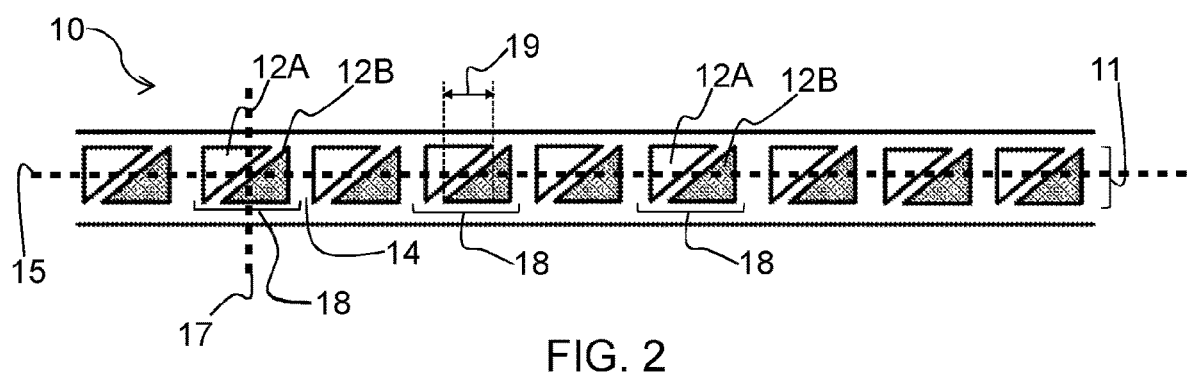
FIG. 2 shows a plan view of a strip of a blister pack according to another example.

As shown in FIG. 2, the series 11 comprises pairs 18 of consecutive blister pockets 12A, 12B. For each pair 18, the pocket 12A containing the first powder medicament and the pocket 12B containing the second powder medicament may overlap each other in the length direction. This may provide a particularly space efficient arrangement of the blister pockets 12A, 12B in the strip 10.

A region of overlap 19 is defined where the consecutive blister pockets 12A, 12B of the pair 18 overlap each other. The width of the blister pocket 12A containing the first powder medicament may decrease in the length direction as the width of the blister pocket 12B containing the second powder medicament increases in the region of overlap 19. In the embodiment of FIG. 2, strip 10 includes a first axis 15 along the length of the strip 10 and a second axis 17 perpendicular to the first axis 15. The first axis 15 and the second axis 17 transect both of the consecutive blister pockets 12A, 12B of the pair 18.

When, for example, the peelable cover 16 covers the blister pockets 12A, 12B, a relatively constant peeling force may be used in order to expose the first and second powder medicaments contained in the blister pockets 12A, 12B of each pair 18. The peeling force is determined by the proportion of the width of the strip in which the base layer 14 is adhered to the cover 16. This means that the decreasing width of the blister pocket 12A of the pair 18 is effectively compensated for by the increasing width of the blister pocket 12B of the pair 18. Such a strip 10 may thus be particularly suitable for use in combination with a peeling mechanism in a dry powder inhaler, which peeling mechanism may exert a relatively constant peeling force during exposing of each pair 18 of blister pockets 12A, 12B.

An overall width of the blister pockets 12A, 12B of the pair 18, as defined by the sum of the widths of the blister pockets 12A, 12B of the pair 18, may be substantially constant in the region of overlap 19. The area in which the peelable cover 16 is adhered to the base layer 14 may be correspondingly substantially constant in the region of overlap 19, and the width of the strip 10 may also be constant along its length. The result may be further improvement the compatibility of the strip 10 with a peeling mechanism of a dry powder inhaler.

Whilst the overlapping pair 18 of blister pockets 12A, 12B are triangular in the plan view provided in FIG. 2, this is not intended to be limiting. Other shapes, e.g. more elaborate shapes, may be employed which mean that the width of the blister pocket 12A containing the first powder medicament decreases in the length direction as the width of the blister pocket 12B containing the second powder medicament increases in the region of overlap 19.

Figure 3:
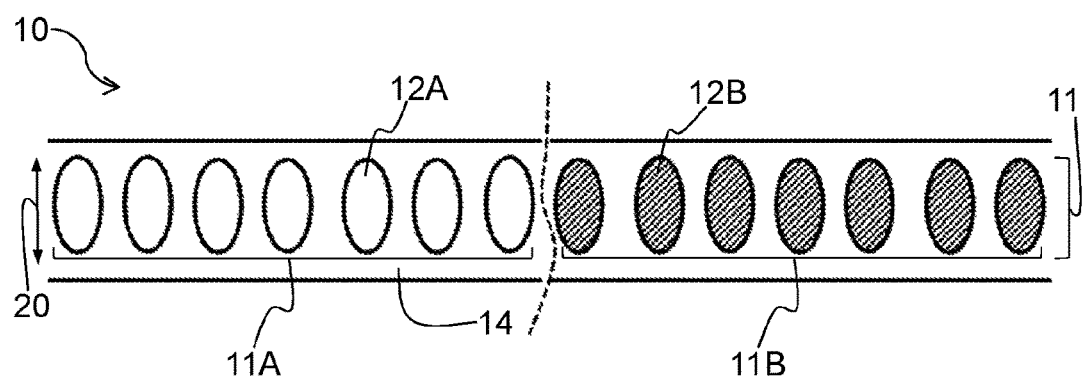
FIG. 3 shows a plan view of a strip of a blister pack according to still another example.

FIG. 3 shows a plan view of a strip 10 according to another non-limiting example. In this case the series 11 comprises a first series 11A of the blister pockets 12A containing the first powder medicament, and a second series 11B of the blister pockets 12B containing the second powder medicament. The first series 11A and the second series 11B are collinear with each other.

The strip 10 may be fabricated, for example, by joining a first precursor strip comprising the first series 11A with a second precursor strip comprising the second series 11B. This may have the advantage of permitting the first and second powder medicaments to be kept separate from each other as the blister pockets 12A, 12B of the respective precursor strips are being filled, thereby to minimize the risk of contamination of the first powder medicament with the second powder medicament, and vice versa.

In another non-limiting example, the first series 11A and the second series 11B are integrally formed in the strip 10. In such an example, a first dispenser may be used to fill the blister pockets 12A of the first series 11A with the first powder medicament, and a second dispenser may be used to fill the blister pockets 12B of the second series 11B with the second powder medicament.

The strip 10 may, for example, comprise a friable portion, such as a perforation, between the first series 11A and the second series 11B. In such an example, a medicament delivery assembly of the dry powder inhaler in which the blister pack is included may be configured to break the friable portion, thereby to separate the first series 11A from the second series 11B prior to accessing the respective blister pockets 12A, 12B of the first series 11A and the second series 11B.

The friable portion may, for instance, be provided by the manner in which the precursor strip in which the first series 11A is defined is joined to the precursor strip in which the second series 11B is defined. Alternatively, the friable portion may be provided in a strip 10 in which the first series 11A and the second series 11B are integrally formed.

In the examples depicted in FIGS. 1A, 1B, and 3, each of the blister pockets 12A, 12B is elongated such as to have a largest dimension parallel with the width of the strip 10. This may assist to achieve a closer spacing between the respective centers of consecutive blister pockets 12A, 12B than, for example, the scenario in which the largest dimension of each of the blister pockets is parallel with the length of the strip 10. In the case of the example shown in FIGS. 1A and 1B, this closer spacing may, in turn, facilitate opening of both of a pair of the consecutive blister pockets 12A, 12B by a medicament delivery assembly included in a dry powder inhaler.

Figure 4A:
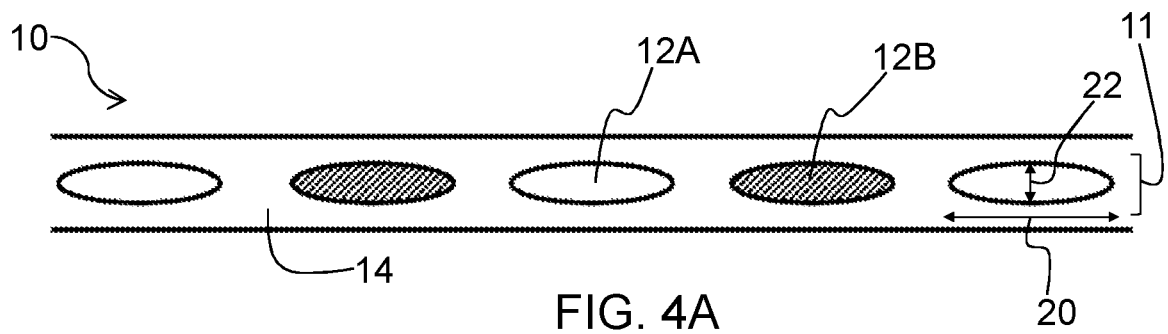
FIG. 4A shows a plan view of a strip of a blister pack according to yet another example.
Figure 4B:
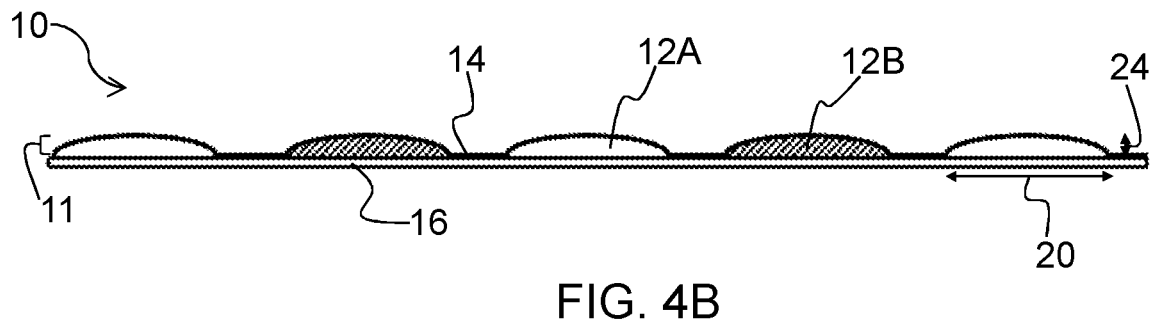
FIG. 4B shows a side view of the strip shown in FIG. 4A.

An alternative non-limiting example is shown in FIGS. 4A and 4B. In this example, the blister pockets 12A containing the first powder medicament, and the blister pockets 12B containing the second powder medicament are arranged in the same series 11 as each other, similarly to the examples shown in FIGS. 1A, 1B, 2, and 3. But in the case of the strip 10 shown in FIGS. 4A and 4B, each of the blister pockets 12A, 12B of the strip 10 is elongated such as to have a largest dimension 20 parallel with the length of the strip 10. This largest dimension 20 is larger than both the maximum width 22 and the maximum depth 24 of each blister pocket 12A, 12B.

Arranging the blister pockets 12A, 12B such that their largest dimension lies parallel with the length of the strip 10 further assists to minimize the width of the strip 10, whilst ensuring that sufficient volume is provided in the blister pockets 12A, 12B to contain the requisite quantities of the first and second powder medicaments.

Figure 5:
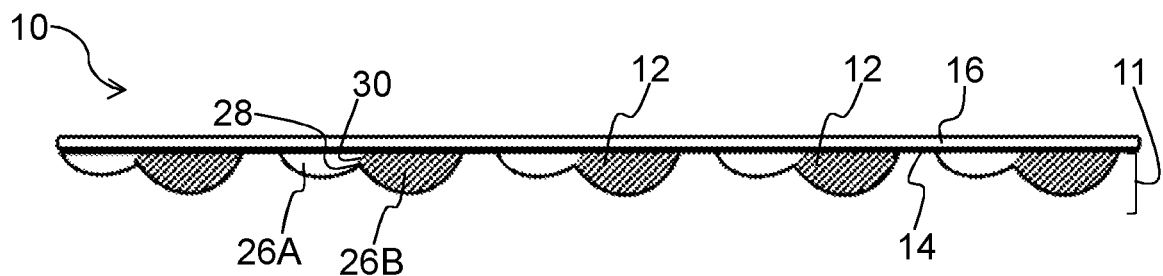
FIG. 5 shows a side view of a strip of a blister pack according to a further example.

FIG. 5 shows a side view of a strip 10 according to a further non-limiting example. In this example, the width of the strip 10 is minimized by virtue of the first powder medicament and the second powder medicament being contained within blister pockets 12 of the same series 11, as well as by each of the blister pockets 12 having their largest dimension 22 parallel with the length of the strip 10. Moreover, each of the blister pockets 12 is divided into a first pocket portion 26A containing the first powder medicament, and a second pocket portion 26B containing the second powder medicament. In the example shown in FIG. 5, the first pocket portion 26A is at a different position along the length of the strip 10 from the second pocket portion 26B.

Each of the blister pockets 12 may provide, for instance, a combined dose of the first and second powder medicaments contained therein. The first and second powder medicaments of the combined dose being contained in adjacent pocket portions 26A, 26B of the same blister pocket 12 may facilitate simultaneous delivery of the first and second powder medicaments by a dry powder inhaler.

As shown in FIG. 5, the first pocket portion 26A adjoins the second pocket portion 26B at a pinch point 28. The pinch point 28 may restricting combining of the first and second powder medicaments with each other. In the example shown in FIG. 5, the pinch point 28 may be configured to minimize a gap 30 between the pinch point 28 and the cover 16. Whilst the first and second powder medicaments may contact each other at the gap 30, the packing of the adjacent pocket portions 26A, 26B, combined with a relatively narrow gap 30, may restrict the degree to which the first and second powder medicaments mix with each other. In this manner, the risk of reactions and/or interactions of the first and second powder medicaments with each other may be minimized.

The first pocket portion 26A may, for instance, contain a different volume of the first powder medicament from that of the second powder medicament contained by the second pocket portion 26B. This is represented in FIG. 5 by the first pocket portion 26A being smaller in the side view than the second pocket portion 26B. In this way, the respective volumes of the pocket portions 26A, 26B may be adjusted according to the dose strengths of the first and second powder medicaments to be delivered to the subject. This may be particularly advantageous when the first and second powder medicaments are to be inhaled simultaneously using a dry powder inhaler.

Figure 6:
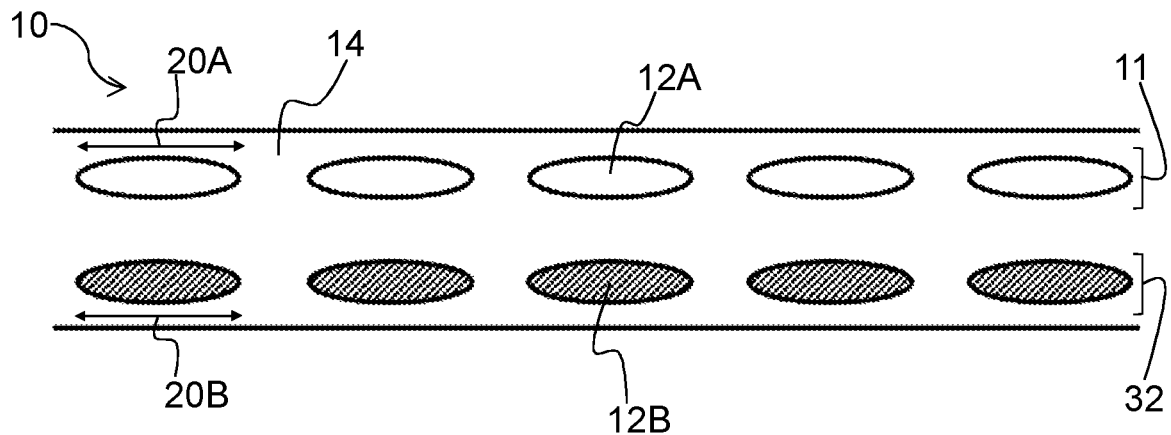
FIG. 6 shows a plan view of a strip of an exemplary blister pack comprising a plurality of linear series of blister pockets.

FIG. 6 shows a plan view of an exemplary strip 10 comprising a series 11 of blister pockets 12A and a further series 32 of blister pockets 12B. Both the series 11 and the further series 32 extend linearly along the length of the strip 10. As shown in FIG. 6, each of the blister pockets 12A, 12B of the series 11 and the further series 32 is elongated such as to have a largest dimension 20A, 20B parallel with the length of the strip 10.

The largest dimension 20A, 20B of the blister pockets 12A, 12B being parallel with the length of the strip for both the series 11 and the further series 32, may assist to minimize the width of the strip 10, in spite of the strip 10 comprising a plurality of series 11, 32 which are spaced apart from each other across the width of the strip 10.

In the non-limiting example shown in FIG. 6, each of the blister pockets 12A of the series 11 contains the first powder medicament, and each of the blister pockets 12B of the further series 32 contains the second powder medicament. This may, for example, facilitate manufacturing of the strip 10, since the first powder medicament may, for instance, be dispensed into the blister pockets 12A of the series 11 defined in a first precursor strip, and the second powder medicament may be dispensed into the blister pockets 12B of the further series 32 defined in a second precursor strip, followed by joining of the first and second precursor strips together along their respective lengths to form the strip 10.

In other non-limiting examples, the blister pockets 12A and the blister pockets 12B may be integrally formed in the strip 10, and a first dispenser may fill the blister pockets 12A with the first powder medicament, and a second dispenser may fill the blister pockets 12B with the second powder medicament.

As shown in FIG. 6, at least part of each of the blister pockets 12A of the series 11 is aligned with a respective blister pocket 12B of the further series 32. In this case, a medicament delivery assembly of a dry powder inhaler may access one of the blister pockets 12A of the series 11 and an aligned blister pocket 12B of the further series 32 for each inhalation using the inhaler. Such accessing may, for example, be effected by peeling a peelable cover 16 to expose the blister pocket 12A and the aligned blister pocket 12B for each inhalation.

Whilst the blister pockets 12A containing the first powder medicament are schematically shown in FIGS. 1A, 1B, 2, 3, 4A, 4B, and 6 (as well as in FIGS. 8A, 8B, 8C described herein below) as having the same dimensions as the blister pockets 12B containing the second powder medicament, this is not intended to be limiting. The blister pockets 12A containing the first powder medicament may have a different volume from the volume of the blister pockets 12B containing the second powder medicament, for example when the first powder medicament is to be delivered at a different dose strength relative to the second powder medicament.

Figure 7A:
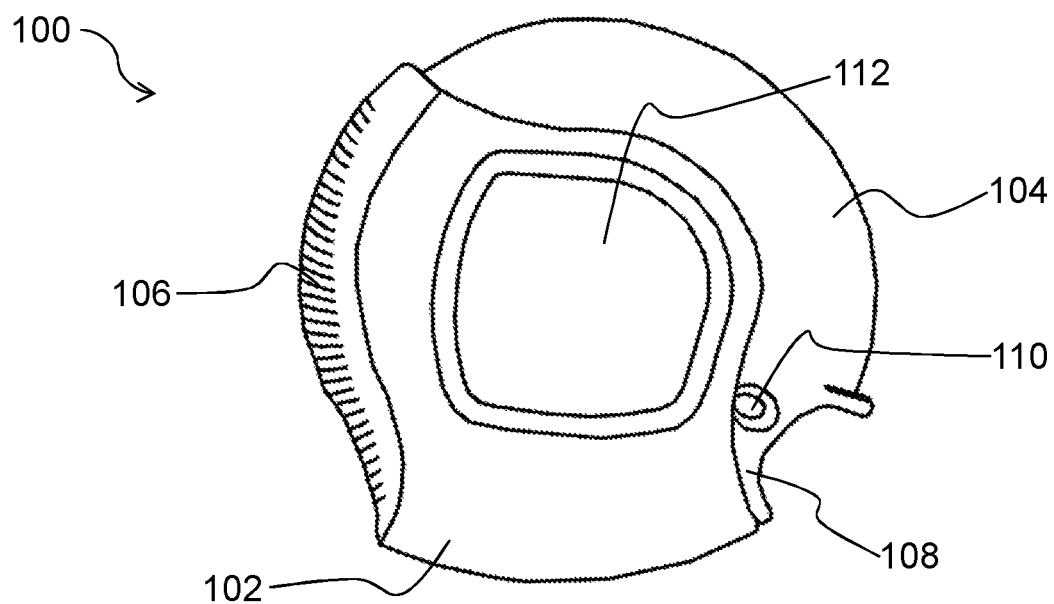
FIG. 7A shows the exterior of a dry powder inhaler according to an example.

FIG. 7A shows the exterior of a dry powder inhaler 100 according to a non-limiting example. The inhaler 100 comprises a first housing part 102 and a second housing part 104. The second housing part 104 is rotatably slidable relative to the first housing part 102. Moreover, the second housing part 104 can be partially received within the first housing part 102 when the housing parts 102, 104 are rotated relative to each other. Thus, the second housing part 104 can be slid partially into first housing part 102, thereby exposing a mouthpiece (not visible in FIG. 7A) and a lever or button for actuating or triggering a medicament delivery assembly (not visible in FIG. 7A) included in the inhaler 100. Subsequently to an inhalation using the inhaler 100 via the mouthpiece, the second housing part 104 can be returned to the position shown in FIG. 7A in which the mouthpiece and the lever/button are covered.

As shown in FIG. 7A, the first housing part 102 may comprise a grip portion 106 to assist the user to expose/cover the mouthpiece. The user may grasp the first housing part 106 and use a digit, such as a finger or thumb, placed in a digit receiving member 108, to slide the second housing part 104 partially into the first housing part 102, thereby to expose the mouthpiece and the lever/button.

The inhaler 100 may further comprise a window 110, in this example delimited by the second housing part 104. In this respect, the inhaler 100 may comprise a dose counter for counting the number of actuations/triggers made via the lever or button. The dose counter may be electronic and/or mechanical, and the number of doses already dosed and/or the number of doses remaining may be displayed by the dose counter. This number of doses may be visible through the window 110.

In a non-limiting example, the strip 10 has numbers printed thereon corresponding to the number of doses. The printed numbers on the strip 10 may align with and be visible through the window 110, thereby to indicate the number of doses of the strip 10 already dosed and/or the number of doses remaining in the strip 10.

The exterior of the inhaler 100 may further comprise a region 112 on which, for example, a medicament label may be affixed. A user interface (not visible in the Figures), for example, comprising one or more light indicators, a touchscreen, and/or buttons for operating electronic circuitry, and so on, may be alternatively or additionally mounted in the region 112. Such a user interface may be used, for instance, to control use detection and wireless connectivity electronics for sending use detection data to an external device, such as a smartphone.

Figure 7B:
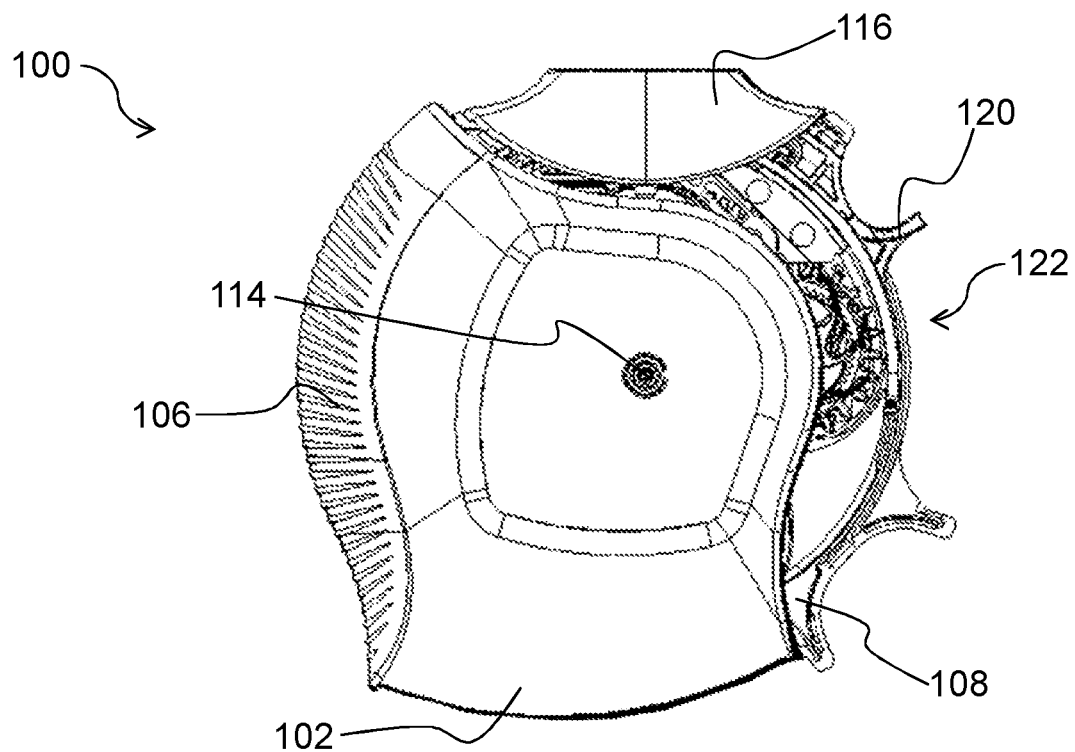
FIG. 7B provides a view of the inhaler shown in FIG. 7A with the housing partially removed.

FIG. 7B provides a view of the inhaler 100 with a portion of the second housing part 104 removed. FIG. 7B shows the pivot point 114 about which the first and second housing parts 102, 104 are rotatable relative to each other, thereby to expose and cover the mouthpiece 116 and the lever 120 of the medicament delivery assembly 122, as previously described.

Figure 7C:
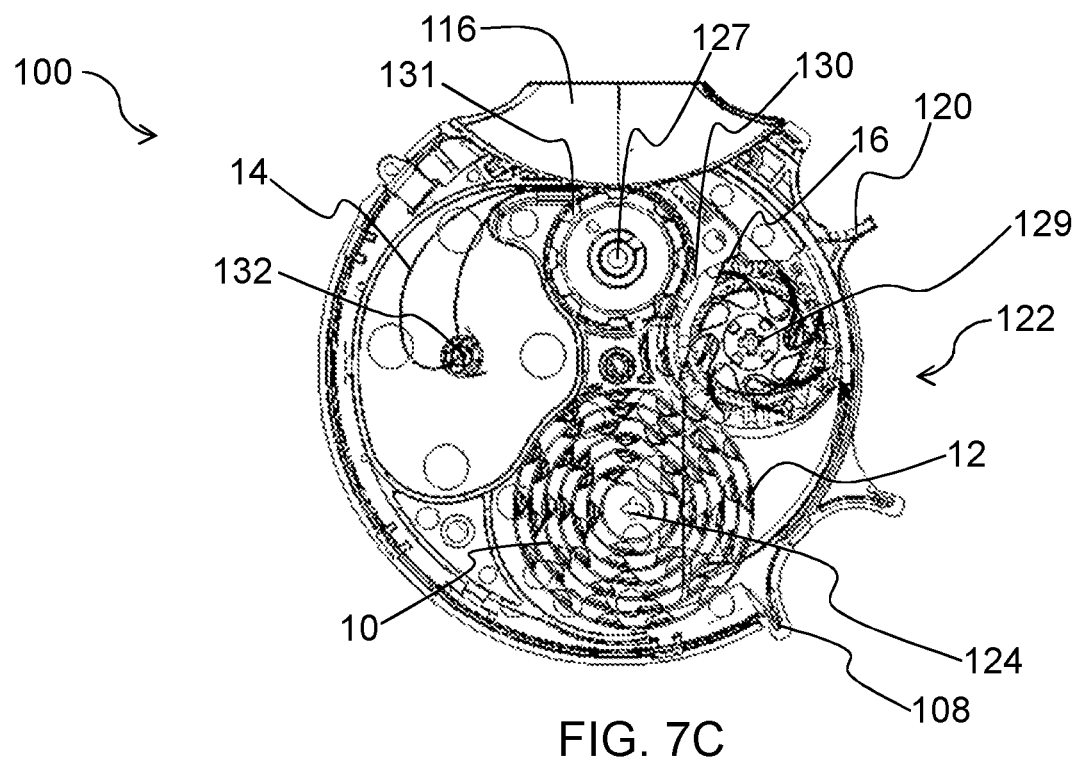
FIG. 7C provides an interior view of the inhaler shown in FIG. 7A.

FIG. 7C provides an interior view of the inhaler 100 when the inhaler 100 is not being actuated. The inhaler 100 comprises a blister pack, for example a blister pack comprising the strip 10 according to any of the above-described examples. The inhaler 100 further comprises a medicament delivery assembly 122 configured to access the blister pockets 12, 12A, 12B and permit a subject to inhale the first and second powder medicaments therefrom.

In this non-limiting example, the strip 10 is incrementally unwound from a spool 124 with each successive actuation of the medicament delivery assembly 122. Actuation of the medicament delivery assembly 122 is effected by the user displacing the lever 120 from its unactuated position shown in FIG. 7C to the actuated position shown in FIG. 7D.

The medicament delivery assembly 122 may, for example, also be configured to return the lever 120 to its unactuated position when the housing parts 102, 104 are rotated relative to each other to (re-)cover the mouthpiece 116 and the lever 120.

Figure 7D:
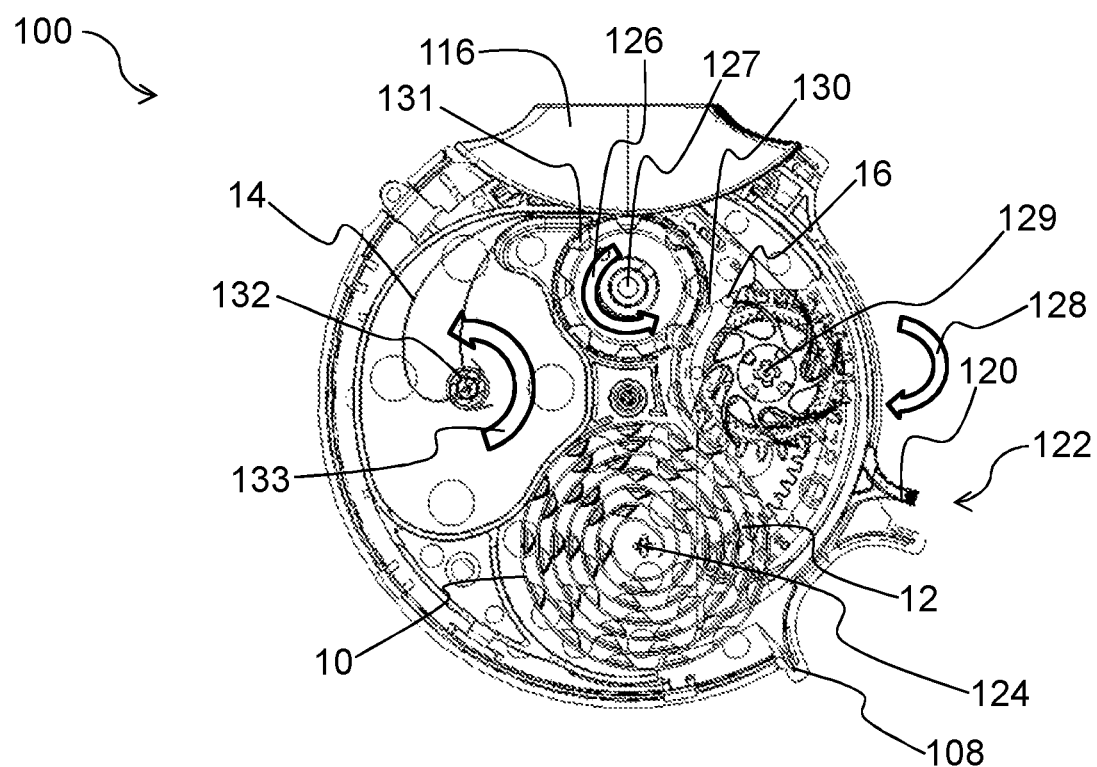
FIG. 7D schematically depicts a blister pocket or pockets being accessed by the inhaler shown in FIG. 7A.

A gearing arrangement, which is only partially visible in FIGS. 7C and 7D, translates movement of the lever 120 to rotation 126 of an indexing wheel 127, and rotation 128 of a waste cover spool 129. As shown in FIG. 7D, the rotation 126 of the indexing wheel 127 is in the opposite direction relative to the rotation 128 of the waste cover spool 129. This causes the peelable cover 16 to be peeled from the base layer 14 at the peeling point 130, thereby exposing the dry powder medicament(s) contained in the blister pockets 12.

The medicament delivery assembly 122 may further comprise a manifold (not visible in the Figures) which is configured such that the dry powder medicaments(s) from the exposed blister pockets 12 is or are drawn therethrough and out of the mouthpiece 116 when the subject inhales through the mouthpiece 116.

As shown in FIG. 7D, the indexing wheel 127 comprises a plurality of recesses 131 around its circumference, which recesses 131 are each dimensioned and/or shaped to receive a blister pocket 12 of the strip 10. Once the subject has inhaled the dry powder medicament(s) from the blister pocket(s) 12 exposed by actuation of the inhaler 100, the spent blister pockets 12 are collected on the waste base layer spool 132. Each actuation using the lever 122 may cause the gearing arrangement to cause the waste base layer spool 132 to rotate, in this case in the same direction 133 as the direction of rotation 126 of the indexing wheel 127. In this manner, the waste base layer 14 is incrementally collected on the waste base layer spool 132 and, concurrently, the waste cover 16 is incrementally collected on the waste cover spool 129.

The effective winding diameter of the waste cover spool 129 may become greater as more waste cover 16 is collected thereon. In order to assist uniform indexing of the strip 10 over its length, the waste cover spool 129 may have a collapsible design, in this example by having a plurality of radial arms which are arranged to collapse inwardly as more of the waste cover 16 is collected on the waste cover spool 129. This may assist to maintain a substantially uniform winding diameter of the waste cover spool 129 as more waste cover 16 is collected thereon.

In alternative examples, the medicament delivery assembly 122 comprises a clutch for adjusting for an increase in the effective winding diameter of the waste cover spool 129 during use of the dry powder inhaler. Alternatively or additionally, the pitch or spacing of the blister pockets 12 may be varied along the length of the strip 10 in order to maintain uniform indexing of the strip 10 over its length.

In other non-limiting examples, the medicament delivery assembly 122 may not access each of the blister pockets 12 by peeling a peelable cover 16 from a base layer 14 in which the blister pockets 12 are defined. Rather, the medicament delivery assembly 122 may comprise a rupturing mechanism, a puncturing mechanism, or a tearing mechanism for accessing the blister pockets 12 by rupturing, puncturing, or tearing respectively.

In an embodiment, the medicament delivery assembly 122 is configured to permit the subject to inhale the first and second powder medicaments simultaneously. In such an embodiment, the medicament delivery assembly 122 may, for instance, be configured such that each actuation of the inhaler 100, for example by movement of the lever 120, causes the peelable cover 16 to be peeled from the base layer 14, thereby to expose a blister pocket 12A containing the first powder medicament, and a blister pocket 12B containing the second powder medicament. The manifold may be arranged such that the subject can inhale the first and second powder medicaments from the thus exposed blister pockets 12A, 12B simultaneously.

The blister pocket 12A containing the first powder medicament and the blister pocket 12B containing the second powder medicament may be, for example, consecutive blister pockets 12A, 12B of the same series 11. In this case, the medicament delivery assembly 122 may peel the peelable cover 16 covering the consecutive blister pockets 12A, 12B during each actuation. In this manner, the medicament delivery assembly 122 may, for example, be configured to access consecutive blister pockets 12A, 12B of the exemplary strips 10 shown in FIGS. 1A, 1B, 2, 4A, and 4B.

In other non-limiting examples, the medicament delivery assembly 122 may be configured to access one blister pocket 12 at a time, for example when combined inhalation of the first and second powder medicaments is not required.

In the case that the strip 10 comprises the elongated blister pockets 12A, 12B whose largest dimension extends parallel with the length of the strip 10, as in the examples shown in FIGS. 4A, 4B, 5 and 6, the medicament delivery assembly 122 may be configured such that at least one of the elongated blister pockets 12A, 12B, 12 is accessed for each inhalation using the inhaler 100.

For example, each actuation of the medicament delivery assembly 122, e.g. via movement of the lever 120, may cause the peelable cover 16 to be peeled back from the base layer 14 to a degree which causes one of the elongated blister pockets 12A, 12B, 12 to be exposed. The manifold may be arranged such that the subject can inhale the powder medicament(s) from the thus exposed blister pocket 12A, 12B, 12.

In the case of the exemplary strip 10 depicted in FIG. 5 being incorporated in the dry powder inhaler 100, the medicament delivery assembly 122 may be configured to access both of the adjoining first and second pocket portions 26A, 26B included in each blister pocket 12 for each inhalation using the inhaler 100. The manifold may be arranged such that the subject can inhale the first and second powder medicaments from the thus exposed pocket portions 26A, 26B simultaneously.

This may be effected by, for example, each actuation of the medicament delivery assembly 122, e.g. via movement of the lever 120, causing the peelable cover 16 to be peeled back from the base layer 14 to a degree which exposes both the first and second pocket portions 26A, 26B of one blister pocket 12.

In the case of the strip 10 comprising the series 11 and the further series 32 of blister pockets, as shown in FIG. 6, the medicament delivery assembly 122 may be configured to access one of the blister pockets 12A of the series 11 and one of the blister pockets 12B of the further series 32 for each inhalation using the inhaler 100. The manifold may be arranged such that the subject can inhale the first and second powder medicaments from the thus exposed blister pockets 12A, 12B of the series 11 and the further series 32 simultaneously.

This may be, for instance, implemented by each actuation of the medicament delivery assembly 122, e.g. via movement of the lever 120, causing the peelable cover 16 to be peeled back from the base layer 14 to a degree which exposes both the first blister pocket 12A of the series 11 and the second blister pocket 12B of the further series 32.

Figure 8A:
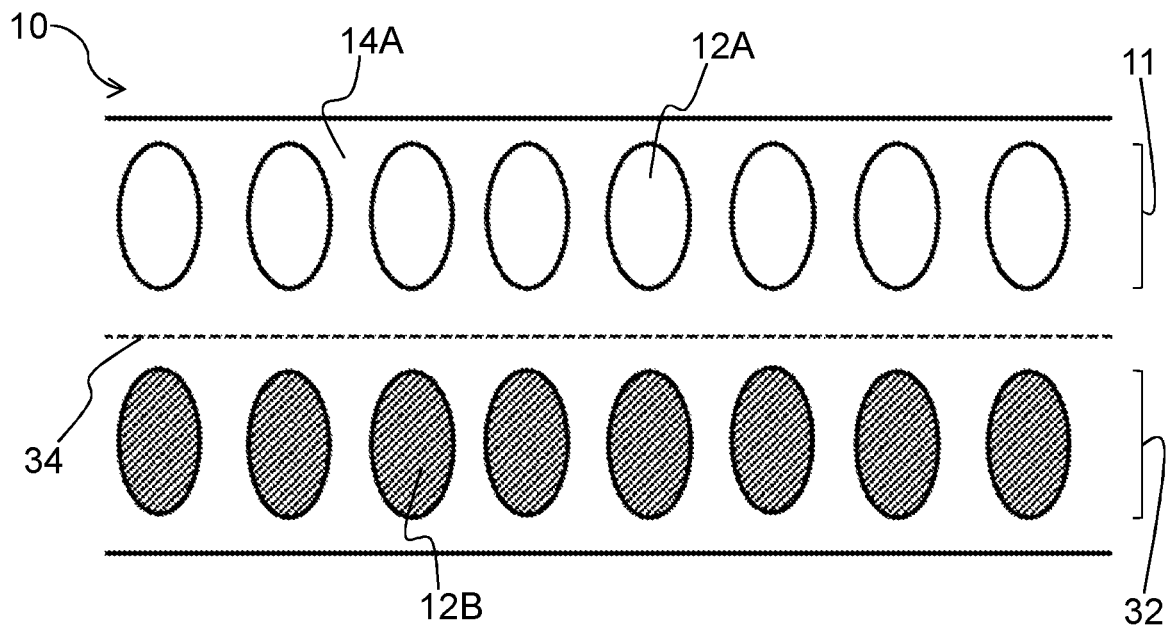
FIG. 8A shows a plan view of a strip of another exemplary blister pack comprising a plurality of linear series of blister pockets.

FIG. 8A shows a plan view of an exemplary strip 10 comprising a plurality of linear series 11, 32 of blister pockets 12A, 12B. In this non-limiting example, a first series 11 and a further series 32 are parallel with each other and extend along the length of the strip 10. Similarly to the example shown in FIG. 6, the first powder medicament is contained in the blister pockets 12A of the series 11, and the second powder medicament is contained in the blister pockets 12B of the further series 32. But the strip 10 shown in FIG. 8A further comprises a friable portion 34 extending along the length of the strip 10 between the series 11 and the further series 32.

Manufacturing of the strip 10 may, for example, comprise dispensing the first powder medicament into the blister pockets 12A of the series 11 defined in a first precursor strip, and the second powder medicament may be dispensed into the blister pockets 12B of the further series 32 defined in a second precursor strip, followed by joining of the first and second precursor strips together along their respective lengths. The friable portion 34 may be provided, for instance, by the manner in which the first and second precursor strips are joined together. Alternatively, the friable portion 34 may be provided in a separate step before or after joining the first and second precursor strips together.

In other non-limiting examples, the blister pockets 12A and the blister pockets 12B may be integrally formed in the strip 10, and a first dispenser may fill the blister pockets 12A with the first powder medicament, and a second dispenser may fill the blister pockets 12B with the second powder medicament. The friable portion 34 may be provided in the strip 10 either before or after filling of the blister pockets 12A, 12B with the first and second powder medicaments.

More generally, the friable portion 34 may comprise, for example, a perforation extending along the length of the strip 10 between the series 11 and the further series 32.

Figure 8B:
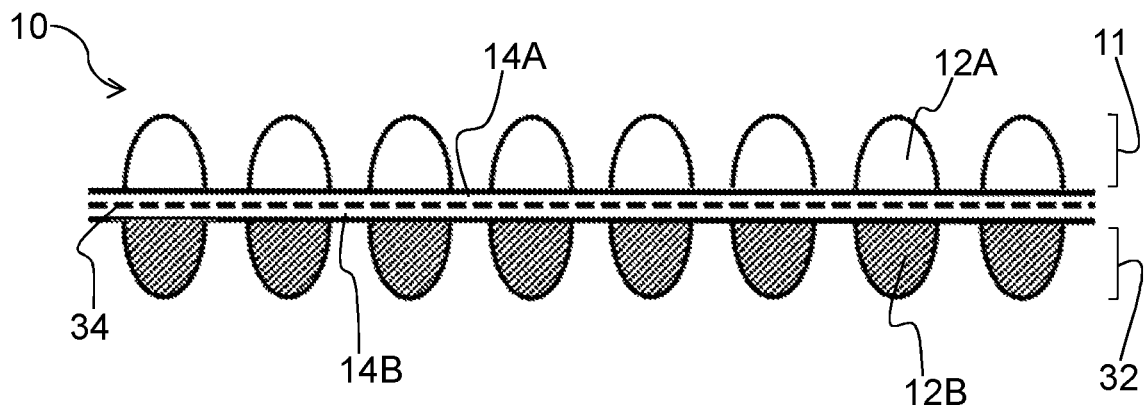
FIG. 8B shows a side view of the strip shown in FIG. 8A when the strip is folded along its length.
Figure 8C:
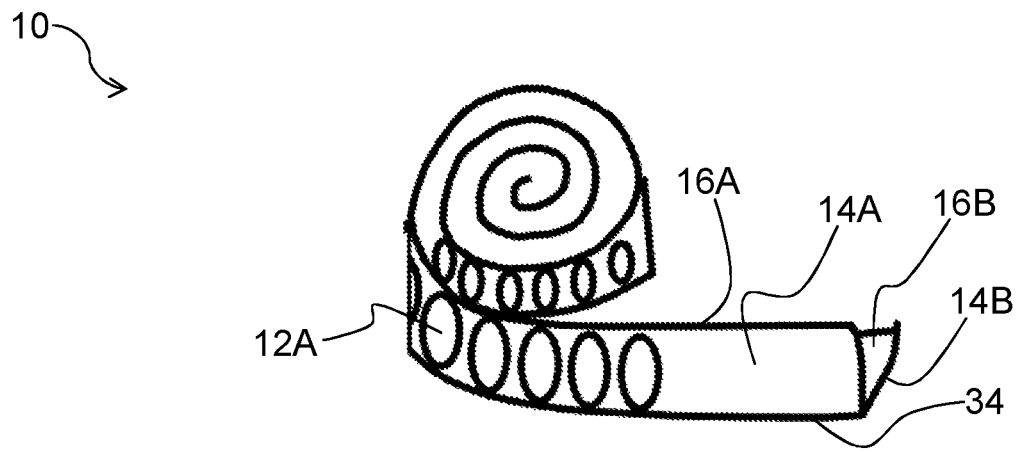
FIG. 8C schematically depicts the strip shown in FIG. 8A in a coiled and folded state.

In an embodiment, the strip 10 is foldable along the friable portion 34. FIG. 8B shows a side view of the strip 10 when the strip 10 is folded along its length along the friable portion 34. By folding the strip 10 in this manner, the base layer 14 may be effectively divided by the friable portion 34 into a first base layer portion 14A comprising the blister pockets 12A of the series 11, and a second base layer portion 14B comprising the blister pockets 12B of the further series 32. FIG. 8C schematically depicts the strip 10 in a coiled and folded state. The strip 10 may be in such a coiled and folded state when, for example, the strip 10 is on the spool 124 included in a medicament delivery assembly 122 of a dry powder inhaler 100.

The medicament delivery assembly 122 may be configured to separate the series 11 from the further series 32 along the friable portion 34. For example, the medicament delivery assembly 122 may be configured to separate the series 11 from the further series 32 prior to accessing the respective blister pockets 12A, 12B of the series 11 and the further series 32.

Figure 9:
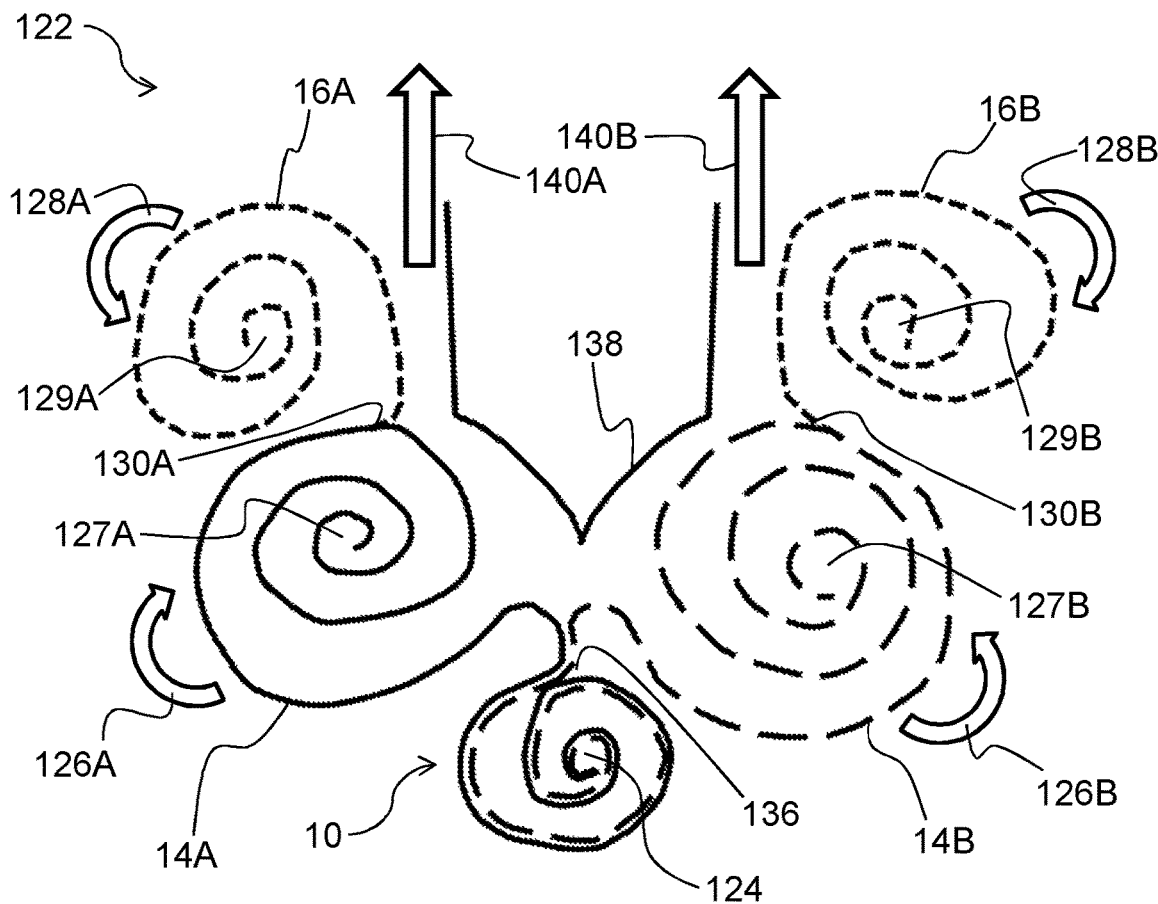
FIG. 9 schematically depicts a dry powder inhaler operating to access blister strips of the strip shown in FIGS. 8A to 8C.

FIG. 9 schematically depicts an exemplary medicament delivery assembly 122 operating to access the blister strips 12A, 12B of the strip 10 shown in FIGS. 8A to 8C. In this non-limiting example, the folded strip 10 is coiled around the spool 124. During actuation of the medicament delivery assembly 122, e.g. by moving the lever 120, the gearing assembly may cause rotation of the first wheel 127A and the second wheel 127B. The direction of rotation 126A of the first wheel 127A may be opposite to the direction of rotation 126B of the second wheel 127B, such that the series 11 and the further series 32 are pulled apart by breaking the friable portion 34 at point 136.

Moreover during the actuation, a first waste cover spool 129A may rotate in a direction 128A which is different from the direction 126A of rotation of the first wheel 127A, thereby to peel a first cover portion 16A from the first base layer portion 14A at point 130A.

Similarly, a second waste cover spool 129B may rotate in a direction 128B which is different from the direction 126B of rotation of the second wheel 127B, thereby to peel a second cover portion 16B from the second base layer portion 14B at point 130B.

Thus, one blister pocket 12A from the series 11 and one blister pocket 12B from the further series 32 may be exposed per actuation of the medicament delivery assembly.

As schematically shown in FIG. 9, the medicament delivery assembly 122 further comprises a manifold 138 which provides fluid communication between the exposed blister pockets 12A, 12B with the mouthpiece 116. The first powder medicament may thus be drawn towards the mouthpiece 116 opening, as represented by the arrow 140A, at the same time as the second powder medicament is drawn towards the mouthpiece 116, as represented by the arrow 140B.

Alternative suitable designs of the medicament delivery assembly 122 which enable separation of the series 11 and the further series 32 along the friable portion 34 are conceivable, such as a medicament delivery assembly 122 comprising a suitable cutting member (not visible in the Figures) for cutting the friable portion along the length of the strip 10. Moreover, it is reiterated that the medicament delivery assembly 122 may be configured to access the blister pockets 12A, 12B in other ways, such as via a rupturing mechanism, a puncturing mechanism, or a tearing mechanism, as previously described.

Figure 10:
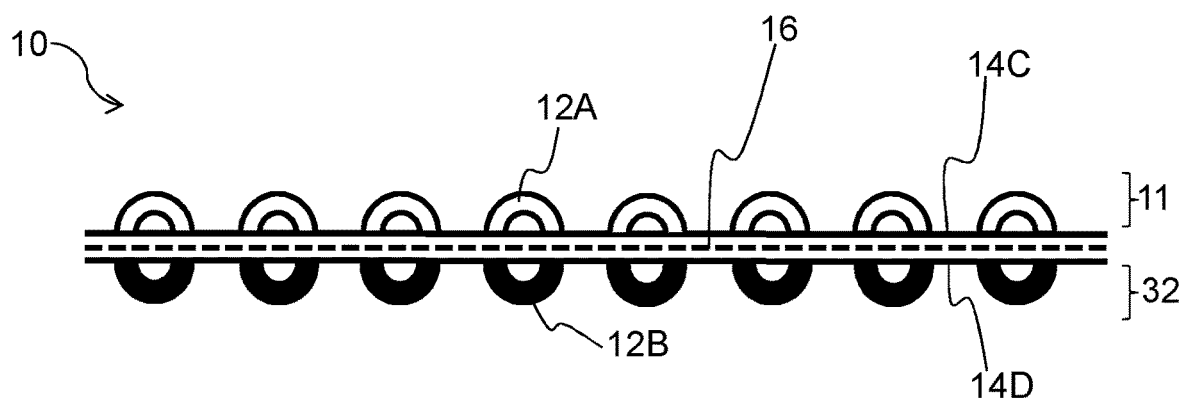
FIG. 10 shows a side view of a strip according to another example.

FIG. 10 shows a side view of a strip 10 according to another example. In this case, the blister pack comprises a first base layer 14C in which a series 11 of blister pockets 12A are defined, and a second base layer 14D in which a further series 32 of blister pockets 12B are defined, the first powder medicament being contained in the blister pockets 12A of the series 11, and the second powder medicament being contained in the blister pockets 12B of the further series 32.

In this non-limiting example, the blister pack further comprises a unitary cover 16, in other words a common lid, for covering the blister pockets of the series 11 and the further series 32.

A single unitary cover 16 can assist to increase the compactness of the dry powder inhaler by (at least) decreasing the thickness of the strip 10 relative to the scenario in which the series 11 and further series 32 of blister pockets of the first and second base layers 14C, 14D are each covered by their own cover.

The unitary cover 16 comprises a first surface and a second surface facing away from the first surface, with the blister pockets 12A of the series 11 being covered by the first surface of the unitary cover 16, and the blister pockets 12B of the further series 32 being covered by the second surface of the unitary cover 16.

Other than the first and second surfaces covering the blister pockets 12A, 12B of the series and the further series 11, 32, the description of the cover 16 provided in relation to the examples described above is applicable to this example.

The medicament delivery assembly included in the dry powder inhaler may be configured to access the blister pockets 12A, 12B of the first and second series 11, 32 and permit a subject to inhale the first and second powder medicaments therefrom.

The blister pockets 12A of the series 11 may be aligned with the blister pockets 12B of the further series 32, as shown in FIG. 10. Alternatively, the blister pockets 12A of the series 11 may be offset relative to the blister pockets 12B of the further series 32. Both of these scenarios are possible due, at least in part, to the unitary cover 16.

In a non-limiting example, the unitary cover 16 is a peelable cover, and the first surface is releasably adhered to the first base layer 14C between the blister pockets 12A of the series 11, and the second surface is releasably adhered to the second base layer 14D between the blister pockets 12B of the further series 32.

In such an example, the medicament delivery assembly can comprise a peeling mechanism configured to peel the first base layer 14C and the second base layer 14D from the unitary cover 16 thereby to expose the first and second powder medicaments.

Peeling the unitary cover 16 from both the first and second base layers 14C, 14D can provide a convenient way of accessing the blister pockets 12A, 12B. The peeling mechanism can, for example, be configured to peel the first base layer 14C and the second base layer 14D from the unitary cover 16 at the same time.

Alternatively, the peeling mechanism can, for example, be configured to peel the first base layer 14C from the unitary cover 16 and then, subsequently, peel the second base layer 14D from the unitary cover 16 (or vice versa).

In other examples, the blister pockets of the series 11 and the further series 32 can be accessed via a suitable rupturing, puncturing and/or tearing mechanism included in the medicament delivery assembly.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A dry powder inhaler configured to deliver a first powder medicament and a second powder medicament different from the first powder medicament, the dry powder inhaler comprising:
   a blister pack; and
   a medicament delivery assembly,
   wherein the blister pack comprises:
      a strip in which blister pockets are defined, said first and second powder medicaments being contained within the blister pockets, wherein a series of blister pockets is defined in the strip, the series extending linearly along a length of the strip,
      wherein the first and second powder medicaments are respectively contained in consecutive blister pockets of the series, such that the blister pockets containing the first powder medicament alternate with and are discrete from the blister pockets containing the second powder medicament along the length of the strip,
      wherein the blister pack further comprises a peelable cover for covering the blister pockets, wherein the blister pockets are defined in a base layer, and wherein the peelable cover is releasably adhered to the base layer between the blister pockets, and wherein the medicament delivery assembly is configured to:
   access the blister pockets and permit a subject to inhale the first and second powder medicaments therefrom,
   wherein the medicament delivery assembly is configured to permit the subject to inhale the first and second powder medicaments simultaneously, the medicament delivery assembly being configured to access consecutive blister pockets for each inhalation using the inhaler,
   wherein the medicament delivery assembly comprises a peeling mechanism configured to peel the cover covering a pair of consecutive blister pockets thereby to expose the first and second powder medicaments for each inhalation using the inhaler,
   wherein both blister pockets in the pair of consecutive blister pockets are transected by a first axis along the length of the strip and by a second axis perpendicular to the first axis.

2. The dry powder inhaler according to claim 1, wherein the blister pockets containing the first powder medicament and the blister pockets containing the second powder medicament are integrally formed in the strip.

3. The dry powder inhaler according to claim 1, wherein the blister pockets are substantially triangular when the strip is viewed in plan.

4. The dry powder inhaler according to claim 3, wherein the blister pockets are substantially triangular in shape.

5. The dry powder inhaler according to claim 1, further comprising a mouthpiece, wherein the medicament delivery assembly comprises a manifold configured such that the first and second powder medicaments from the accessed consecutive blister pockets are drawn simultaneously therethrough and out of the mouthpiece when the subject inhales through the mouthpiece.

6. The dry powder inhaler according to claim 5, wherein the manifold comprises a first flow path along which the first powder medicament is carried towards the mouthpiece from one of the accessed consecutive blister pockets, and a second flow path along which the second powder medicament is carried towards the mouthpiece from the other of the accessed consecutive blister pockets.

7. The dry powder inhaler according to claim 1, wherein the medicament delivery assembly is configured to advance the strip by pulling or by pushing the strip.

8. The dry powder inhaler according to claim 1, wherein:
   the first powder medicament comprises budesonide and the second powder medicament comprises formoterol; or
   the first powder medicament comprises beclomethasone and the second powder medicament comprises formoterol; or
   the first powder medicament comprises fluticasone and the second powder medicament comprises salmeterol, or
   the first powder medicament comprises fluticasone and the second powder medicament comprises albuterol, or
   the first powder medicament comprises fluticasone and the second powder medicament comprises vilanterol, or
   the first powder medicament comprises umeclidinium and the second powder medicament comprises vilanterol, or
   the first powder medicament comprises two selected from umeclidinium, fluticasone and vilanterol, and the second powder medicament comprises the remaining medicament from umeclidinium, fluticasone and vilanterol not selected for the first powder medicament.

9. The dry powder inhaler according to claim 1, wherein:
   the first powder medicament comprises fluticasone furoate and the second powder medicament comprises vilanterol trifenatate, or
   the first powder medicament comprises umeclidinium bromide and the second powder medicament comprises vilanterol trifenatate, or
   the first powder medicament comprises two selected from umeclidinium bromide, fluticasone furoate and vilanterol trifenatate, and the second powder medicament comprises the remaining medicament from umeclidinium bromide, fluticasone furoate and vilanterol trifenatate not selected for the first powder medicament.

10. The dry powder inhaler according to claim 1, wherein each blister pocket in the pair of consecutive blister pockets includes a shape in a plan view that includes at least one linear edge.

11. The dry powder inhaler according to claim 10, wherein the at least one linear edge of adjacent pockets in the pair of consecutive blister pockets are oriented parallel to one another.

12. The dry powder inhaler according to claim 11, wherein the at least one linear edge of adjacent pockets of the pair of consecutive blister pockets are disposed along the strip at an angle such that the at least one linear edge is neither parallel nor perpendicular to either of the first axis or the second axis.

13. The dry powder inhaler according to claim 1, wherein each blister pocket in the pair of consecutive blister pockets define substantially the same volume.

14. The dry powder inhaler according to claim 1, wherein each blister pocket in the pair of consecutive blister pockets has a dimensional extent parallel with a width of the strip that varies along the first axis.

15. The dry powder inhaler according to claim 14, wherein the dimensional extent of one of the blister pockets in each pair of blister pockets increases along the first axis and the dimensional extent of the other blister pocket in each pair of blister pockets decreases along a length direction of the first axis.

16. The dry powder inhaler according to claim 15, wherein along the first axis, the dimensional extent in a width direction of the width of the strip of one of the blister pockets in the pair of blister pockets increases and the dimensional extent in the width direction of the width of the strip of the other of the blister pockets in the pair of blister pockets decreases.

17. The dry powder inhaler according to claim 1, wherein consecutive pairs of blister pockets along the strip are each transected by the first axis and each blister pocket in consecutive pairs of blister pockets are transected by a respective second axis, each respective second axis being parallel to each other and perpendicular to the first axis.

18. The dry powder inhaler according to claim 1, wherein, for each said consecutive pair of blister pockets, the pocket containing the first powder medicament and the pocket containing the second powder medicament overlap each other along the first axis.

* * * * *